(12) United States Patent
McNiece et al.

(10) Patent No.: US 11,642,377 B2
(45) Date of Patent: May 9, 2023

(54) BONE MARROW DERIVED NEUROKININ-1 RECEPTOR POSITIVE (NK1R+) MESENCHYMAL STEM CELLS FOR THERAPEUTIC APPLICATIONS

(71) Applicant: BioCardia, Inc., San Carlos, CA (US)

(72) Inventors: Ian McNiece, Coral Gables, FL (US); Peter Altman, Menlo Park, CA (US)

(73) Assignee: BioCardia, Inc., Sunnyvale, CA (US)

( * ) Notice: Subject to any disclaimer, the term of this patent is extended or adjusted under 35 U.S.C. 154(b) by 173 days.

(21) Appl. No.: 16/583,721

(22) Filed: Sep. 26, 2019

(65) Prior Publication Data

US 2020/0101113 A1   Apr. 2, 2020

Related U.S. Application Data

(60) Provisional application No. 62/737,627, filed on Sep. 27, 2018.

(51) Int. Cl.
| | |
|---|---|
| *A61K 35/28* | (2015.01) |
| *A61P 9/10* | (2006.01) |
| *C12N 5/0775* | (2010.01) |
| *C12N 5/077* | (2010.01) |

(52) U.S. Cl.
CPC ............ *A61K 35/28* (2013.01); *A61P 9/10* (2018.01); *C12N 5/0657* (2013.01); *C12N 5/0663* (2013.01); *C12N 2502/1394* (2013.01)

(58) Field of Classification Search
CPC ......... A61K 35/28; A61P 9/10; C12N 5/0657; C12N 5/0663; C12N 2502/1394
See application file for complete search history.

(56) References Cited

U.S. PATENT DOCUMENTS

| | | | |
|---|---|---|---|
| 2014/0023621 A1 | 1/2014 | Hare et al. | |
| 2014/0065109 A1 | 3/2014 | Son et al. | |

FOREIGN PATENT DOCUMENTS

| | | |
|---|---|---|
| WO | WO-2020069215 | 4/2020 |

OTHER PUBLICATIONS

Kuei et al. Clonal analysis of multipotent stromal cells derived from CD271+ bone marrow mononuclear cells: functional heterogeneity and different mechanisms of allosuppression. Haematologica. 98(10), p. 1609-1616 (Year: 2013).*
Zhang et al. Endothelial precursor cells stimulate pericyte-like coverage of bone marrow-derived mesenchymal stem cells through platelet-derived growth factor-BB induction, which is enhanced by substance P. Microcirculation. 2017;24:e12394. p. 1-9 (Year: 2017).*
See et al. Therapeutic effects of human STRO-3-selected mesenchymal precursor cells and their soluble factors in experimental myocardial ischemia. J. Cell. Mol. Med. vol. 15, No. 10, 2011 pp. 2117-2129 (Year: 2011).*
van der Kleij et al. Functional Expression of Neurokinin 1 Receptors on Mast Cells Induced by IL-4 and Stem Cell Factor. The Journal of Immunology, 2003, 171: 2074-2079 (Year: 2003).*
Liew et al. Endothelial progenitor cells: diagnostic and therapeutic considerations. BioEssays 28:261-270 (Year: 2006).*
Jin et al. Substance P enhances mesenchymal stem cells-mediated immune modulation. Cytokine 71 (2015) 145-153 (Year: 2015).*
Hong et al. Substance-p-mobilized Mesenchymal Stem Cells Accelerate Skin Wound Healing. Tissue Engineering and Regenerative Medicine, vol. 11, No. 6, pp. 483-491 (Year: 2014).*
Almeida et al. Wnt proteins prevent apoptosis of both uncommitted osteoblast progenitors and differentiated osteoblasts by beta-catenin-dependent and -independent signaling cascades involving Src/ERK and phosphatidylinositol 3-Kinase/AKT. JBiol. Chem. 280:41342-41351 (2005).
Alvarez-Buyalla et al. Identification of neural stem cells in the adult vertebrate brain. Brain Res. Bull. 57:751-758 (2002).
Barnabe-Heider et al. Evidence that embryonic neurons regulate the onset of cortical gliogenesis via cardiotrophin-1. Neuron 48:253-265 (2005).
Beattie et al. Activin A maintains pluripotency of human embryonic stem cells in the absence of feeder layers. Stem Cells 23:489-495 (2005).
Buytaert-Hoefen et al. Generation of tyrosine hydroxylase positive neurons from human embryonic stem cells after coculture with cellular substances and exposure to GDNF. Stem Cells 22:669-674 (2004).
Davis et al. Local myocardial insulin-like growth factor 1 (IGF-1) delivery with biotinylated peptide nanofibers improves cell therapy for myocardial infarction. Proc. Natl. Acad. Sci. USA103: 8155-8160 (2006).
Dawn et al. Cardiac stem cells delivered intravascularly traverse the vessel barrier, regenerate infarcted myocardium, and improve cardiac function. Proc. Natl. Acad. Sci. USA 102, 3766-3771 (2005).
Dubon, et al. Substance P enhances the proliferation and migration potential of murine bone marrow-derived mesenchymal stem cell-like cell lines. Experimental and Therapeutic Medicine 9: 1185-1191, 2015.
Encabo et al. Selective generation of different dendritic cell precursors from CD34+ cells by interleukin-6 and interleukin-3. Stem Cells 22:725-740 (2004).
Fiordaliso et al. Hyperglycemia activates p53 and p53-regulated genes leading to myocyte cell death. Diabetes 50: 2363-2375 (2001).
Greco et al. Enhancing effect of il-1 alpha on neurogenesis from adult human mesenchymal stem cells: implication for inflammatory mediators in regenerative medicine. J. Immunol. 179(5): 3342-3350 (2007).
He et al. Paracrine mitogenic effect of human endothelial progenitor cells: role of interleukin-8. Am J. Physiol. 289:H968-H972 (2005).
Heese et al. Neural stem cell migration toward gliomas in vitro. Neuro-oncol. 7:476-484 (2005).

(Continued)

*Primary Examiner* — Taeyoon Kim
(74) *Attorney, Agent, or Firm* — Wilson Sonsini Goodrich & Rosati

(57) ABSTRACT

The present disclosure provides use of neurokinin 1 receptor (NK1R) as a marker for identifying and/or isolating multipotential cells. The present disclosure provides cell populations enriched by methods of the present disclosure and therapeutic uses of these cells and agents derived from these cells.

16 Claims, 5 Drawing Sheets

(56) References Cited

OTHER PUBLICATIONS

Kajstura et al. IGF-1 overexpression inhibits the development of diabetic cardiomyopathy and angiotestin II-mediated oxidative stress. Diabetes 50: 1414-1424 (2001).
Kamanga-Sollo et al. Insulin-like growth factor binding protein (IGFBP)-3 and IGFBP-5 mediate TGF-beta and myostatin-induced suppression of proliferation in porcine embryonic cells. Exp Cell Res 311:167-176 (2005).
Kanemura et al. In vitro screening of exogenous factors for human neural stem/progenitor cell proliferation using measurement of total atp content in viable cells. Cell Transplant 14:673-682 (2005).
Kaplan et al. VEGFR1-positive haematopoietic bone marrow progenitors initiate the pre-metastatic niche. Nature438:820-827(2005).
Kobayashi et al. Endothelial progenitor cell differentiation and senescence in angiotensin II-infusion rat model. Hypertens.Res. 29:449-455 (2006).
Kollet et al. HGF, SDF-1, and MMP-9 are involved in stress-induced human CD34+ stem cell recruitment to the liver. J.Clin. Invest. 112:160-169 (2003).
Leri et al. Stretch-mediated release of angiotesin II induces myocyte apoptosis by activating p53 that enhances the local renin-angiotesin system and decreases the Bcl-2-to-Bax protein ration in the cell. J. Clin. Invest. 101: 1326-1342 (1998).
Linke et al. Stem cells in the dog heart are self renewing, clonogenic, and multipotent and regenerate infarcted myocardium, improving cardiac function. Proc.Natl. Acad. Sci. USA 102:8966-8971 (2005).
Liu et al. Substance p promotes the proliferation, but inhibits differentiation and mineralization of osteoblasts from rats with spinal cord injury via rankl/opg system. PLoS One 11(10): 1-18 (2016).
Madlambayan et al. Dynamic changes in cellular and microenvironmental composition can be controlled to elicit in vitro human hematopoietic stem cell expansion. Exp Hematol 33: 1229-1239 (2005).
McMurray et al. Effects of candesartan in patients with chronic heart failure and reduced left-ventricular systolic function taking angiotensin-converting-enzyme inhibitors: the CHARM-added trial. Lancet362: 767-771 (2003).
Murrell et al. Multipotent stem cells from adult olfactory mucosa. Dev.Dyn. 233:496-515(2005).
Patel et al. Surgical treatment for congestive heart failure with autologous adult stem cell transplantation: a prospective randomized study. TheJournal of Thoracic and Cardiovascular Surgery 130:1631-38 (2005).
PCT/US19/53293 International Search Report dated Dec. 16, 2019.
Perin et al. Transendocardial, autologous bone marrow cell transplantation for severe, chronic ischemic heart failure. Circulation107: 2294-2302 (2003).
Quinn et al. Mouse trophoblast stem cells. Methods Mol. Med. 121:125-148 (2005).
Ratajczak et al. A hypothesis for an embryonic origin of pluripotent Oct-4+ stem cells in adult bone marrow and other tissues. Leukemia21(5):860-867 (2007).
Ribacka et al. Cancer, stem cells, and oncolytic viruses. Ann. Med. epub ahead of print: 1-10 (2008).
Rosu-Myles et al. A unique population of bone marrow cells migrates to skeletal muscle via hepatocyte growth factor/c-met axis. J.Cell. Sci. 118: 4343-4352 (2005).
Sekiya et al. Comparison of effect of BMP-2, -4, and -6 on in vitro cartilage formation of human adult stem cells from bone marrow stroma. Cell Tissue Res 320:269-276 (2005).
Shackleton, et al. Generation of a functional mammary gland from a single stem cell. Nature.Jan. 5, 2006;439(7072):84-8.doi: 10.1038/nature04372.
Sherman. Cellular therapy for chronic myocardial disease: nonsurgical approaches. BasicAppl. Myol. 13: 11-14 (2003).
Torella et al. Cardiac stem cell and mycoyte aging, heart failure, and insulin-like growth factor-1 overexpression. Circ.Res. 94:514-524 (2004).
Urbanek et al. Cardiac stem cells possess growth factor-receptor systems that after activation regenerate the infarcted myocardium, improving ventricular function and long-term survival. Circ.Res. 97:663-673 (2005).
Weidt et al. Differential effects of culture conditions on the migration pattern of stromal cell-derived factor-stimulated hematopoietic stem cells. Stem Cells 22:890-896 (2004).
Xu. In vitro introduction of trophoblast from human embryonic stem cells. Methods Mol. Med. 121:189-202 (2005).
Zuk, et al. Multilineage Cells from Human Adipose Tissue: Implications for Cell-Based Therapies. Tissue Engineering 7(2):211-228 (2001).
Amadesi, Silvia et al. Role for Substance P-Based Nociceptive Signaling in Progenitor Cell Activation and Angiogenesis During Ischemia in Mice and in Human Subjects. Circulation, vol. 125, No. 14 (2012).
Cho, Dong et al. The optimization of cell therapy by combinational application with apicidin-treated mesenchymal stem cells after myocardial infarction. Oncotarget, pp. 44281-44294 (2017).
Douglas, et al. Neurokinin-1 receptor, functional significance in the immune system in reference to selected infections and inflammation. Ann NY Acad Sci 2011;1217:83.
Hong, et al. Anew role of substance P as an injury-inducible messenger for mobilization ofCD29+ stromal-like cells. Nature Medicine vol. 15, pp. 425-435(2009).
Jones, et al., Isolation and characterization of bone marrow multipotential mesenchymal progenitor cells. Arthritis Rheum 2002; 46:3349-3360.
Mei, et al. Neuropeptide SPactivates the WNT signal transduction pathway and enhances the proliferation of bone marrow stromal stem cells. Cell Biology International. Nov. 2013, vol. 37(11):1145-1266.
Munoz, Miguel, et al. Immunolocalization of Substance P and NK-1 Receptor in ADIPOSE Stem Cells. Journal of Cellular Biochemistry, vol. 118, No. 12 (2017).
Supplemental European Search Report for EP19864642 dated Jan. 25, 2022.
Wang, et al. Comprehensive proteomic analysis of exosomes derived from human bone marrow, adipose tissue, and umbilical cord mesenchymal stem cells. Stem Cell Research & Therapy. (2020) 11:511.
Wang, L, et al. Substance P stimulates bone marrow stromal cell osteogenic activity, osteoclast differentiation, and resorption activity in vitro. BONE, vol. 45, No. 2 (2009).
Williams et al. Enhanced Effect of combining Human Cardiac Stem Cells and Bone Marrow Mesenchymal Stem Cells to Reduce Infarct Size and to Restore Cardiac Function After Myocardial infarction Clinical Perspective. Circulation, vol. 27, No. 2 (2012).

* cited by examiner

BONE MARROW DERIVED NEUROKININ-1 RECEPTOR POSITIVE (NK1R+) MESENCHYMAL STEM CELLS FOR THERAPEUTIC APPLICATIONS

CROSS-REFERENCE

This application claims the benefit of U.S. Provisional Application No. 62/737,627, filed Sep. 27, 2018, which application is incorporated herein by reference.

BACKGROUND OF THE INVENTION

Stem cells. Stem cells show potential for many different areas of health and medical research. Some of the most serious medical conditions, such as cancer and birth defects, are caused by problems that occur somewhere in the process of stem cell differentiation or maintenance. Broadly, there are two different types of stem cells, embryonic stem cells and adult stem cells. Embryonic stem cells are found in blastocysts and have the ability to differentiate into all of the specialized embryonic tissues. Adult stem cells are undifferentiated cells found throughout the body after embryonic development. Adult stem cells are able to divide and replenish dying cells and regenerate damaged tissue. Furthermore, adult stem cells can maintain the normal turnover of regenerative organs such as blood, skin and intestinal tissue. Adult stem cells have the ability to divide and self-renew indefinitely and are able to generate all of the cell types of the organ from which they originate.

Stem cells can be classified as being totipotent, pluripotent, multipotent or unipotent based on their potential to differentiate into different cell types. Totipotent stem cells are produced from the fusion of gametes and the first few divisions of the fertilized egg. These cells can differentiate into embryonic and extra-embryonic cell types. Pluripotent stem cells can differentiate into cells from any of the three germ layers. Multipotent calls can produce only cells of a closely related family. Unipotent cells can produce only one cell type, but have the property of self-renewal which distinguishes them from non-stem cells. Most adult stem cells are lineage restricted multipotent stem cells, and are referred to by their tissue of origin. Pluripotent adult stem cells are rare and generally small in number but can be found in a number of tissues including umbilical cord blood (Ratajczak M. Z., et al., *Leukemia* 21(5): 860-867 (2007)). There are several different types of adult stem cells including, but not limited to, adipose derived stem cells (Zuk, P. A., et al., *Tissue Engineering* 7:211-216 (2001)), epithelial stem cells, hematopoietic stem cells, mammary stem cells (Shackleton, M., et al., *Breast Cancer R E.* 7:86-95 (2005)), mesenchymal stem cells, endothelial stem cells, neural stem cells (Alvarez-Bullta, A., et al., *Brain Res. Bull.* 57:751-758 (2002)), olfactory stem cells (Murrel, W., et al., *Dev. Dyn.* 233:496-515 (2005)), testicular stem cells, dental pulp derived stem cells, and umbilical cord blood hematopoietic progenitor cells.

When an adult stem cell divides, it creates another cell like itself and a cell more differentiated than itself. This process of asymmetric cell division, gives rise to one identical daughter cell and one early transient-amplifying cell (early TA), which possesses high proliferative capacity. Through a series of cell divisions, the early TA cell gives rise to a late TA cell followed by a tissue-specific progenitor cell and finally to the bulk of differentiated cells that make up the organ or tissue (Ribacka, C., et al. *Ann. Med.* epub ahead of print: 1-10 (2008)).

Mesenchymal Stem Cells.

Mesenchymal stem cells are multipotent stromal cells that can differentiate into a variety of cell types, including osteoblasts (bone cells), chondrocytes (cartilage cells), myocytes (muscle cells) and adipocytes (fat cells which give rise to marrow adipose tissue). Mesenchymal stem cell based therapeutic clinical trials are in progress, including trials with unselected mesenchymal stem cells and STRO-1 selected mesenchymal stem cells. The name "STRO-1" consists of STRO, which means mesenchyme, and "1", which means it's the first isolated monoclonal antibody to identify mesenchymal stem cells. Mesenchymal stem cells are a mixture of cell subtypes and STRO-1 positive cells are only one of these subtypes, without known signaling involvement in disease.

Substance P.

Substance P (SP) is a neuropeptide released from sensory nerves and is associated with inflammatory processes and pain. The endogenous receptor for substance P is neurokinin 1 receptor (NK1-receptor, NK1R), which is distributed over cytoplasmic membranes of many cell types (for example, neurons, glia, endothelia of capillaries and lymphatics, fibroblasts, stem cells, and white blood cells) in many tissues and organs. SP amplifies or excites most cellular processes.

Elevation of serum, plasma, or tissue SP and/or its receptor (NK1R) has been associated with many diseases: sickle cell crisis, inflammatory bowel disease, major depression and related disorders, fibromyalgia rheumatological, and infections such as HIV/AIDS and respiratory syncytial virus, as well as in cancer. When assayed in the human, the observed variability of the SP concentrations are large, and in some cases the assay methodology is questionable. SP concentrations cannot yet be used to diagnose disease clinically or gauge disease severity. It is not yet known whether changes in concentration of SP or density of its receptors is the cause of any given disease, or an effect.

Substance P is a potent vasodilator. Substance P-induced vasodilatation is dependent on nitric oxide release. Substance P is involved in the axon reflex-mediated vasodilatation to local heating and wheal and flare reaction. It has been shown that vasodilatation to substance P is dependent on the NK1 receptor located on the endothelium. In contrast to other neuropeptides studied in human skin, substance P-induced vasodilatation has been found to decline during continuous infusion. This possibly suggests an internalization of NK1R. As is typical with many vasodilators, it also has bronchoconstrictive properties, administered through the non-adrenergic, non-cholinergic nervous system (branch of the vagal system).

SP initiates expression of almost all known immunological chemical messengers (cytokines). Also, most of the cytokines, in turn, induce SP and the NK1 receptor. SP is particularly excitatory to cell growth and multiplication via usual, as well as oncogenic driver. SP is a trigger for nausea and emesis, Substance P and other sensory neuropeptides can be released from the peripheral terminals of sensory nerve fibers in the skin, muscle, and joints. It is proposed that this release is involved in neurogenic inflammation, which is a local inflammatory response to certain types of infection or injury.

Preclinical data support the notion that Substance P is an important element in pain perception. The sensory function of substance P is thought to be related to the transmission of pain information into the central nervous system. Substance P coexists with the excitatory neurotransmitter glutamate in primary afferents that respond to painful stimulation. Substance P and other sensory neuropeptides can be released from the peripheral terminals of sensory nerve fibers in the skin, muscle, and joints. It is proposed that this release is involved in neurogenic inflammation, which is a local inflammatory response to certain types of infection or injury. Unfortunately, the reasons why NK1 receptor antagonists (NK1RAs) have failed as efficacious analgesics in well-conducted clinical proof of concept studies have not yet been persuasively elucidated.

Substance P has been associated with the regulation of mood disorders, anxiety, stress, reinforcement, neurogenesis, respiratory rhythm, neurotoxicity, pain, and nociception.

The vomiting center in the medulla called the Area Postrema, contains high concentrations of substance P and its receptor, in addition to other neurotransmitters such as choline, histamine, dopamine, serotonin, and opioids. Their activation stimulates the vomiting reflex. Different emetic pathways exist, and substance P/NK1R appears to be within the final common pathway to regulate vomiting.

The above processes are part and parcel to tissue integrity and repair. Substance P has been known to stimulate cell growth in normal and cancer cell line cultures, and it was shown that substance P could promote wound healing of non-healing ulcers in humans. SP and its induced cytokines promote multiplication of cells required for repair or replacement, growth of new blood vessels and "leg-like pods" on cells (including cancer cells) bestowing upon them mobility and metastasis.

The SP-NK1R system induces or modulates many aspects of the immune response, including white blood cell (WBC) production and activation, and cytokine expression. Reciprocally, cytokines may induce expression of SP and its NK1R. In this sense, for diseases in which a pro-inflammatory component has been identified or strongly suspected, and for which current treatments are absent or in need of improvement, abrogation of the SP/NK1R system continues to receive focus as a treatment strategy. Currently, the only completely developed method available in that regard is antagonism (blockade, inhibition) of the SP preferring receptor, i.e., by drugs known as neurokinin type 1 antagonists (also termed: SP antagonists, or tachykinin antagonists.) The SP antagonists have used in the treatment of nausea in chemotherapy.

Recent studies have shown that substance P acts as an injury inducible messenger for mobilization of CD29+ stromal like cells [Hong 2009], enhances the proliferation of bone marrow stromal cells [Mei 2013], enhances the proliferation and migration potential of murine bone marrow derived mesenchymal stem-like cell lines [Dubon 2015].

SUMMARY OF THE INVENTION

Cardiovascular disease, such as ischemic cardiomyopathy, remains as a major health issue in which effective treatment is currently needed. The present disclosure addresses such needs and provides a number of advantages. The present disclosure provides compositions comprising mesenchymal stem cells to treat various diseases and disorders, such as cardiovascular disease. The present disclosure identifies the therapeutic promise in the population of mesenchymal and mesenchymal precursor stem cells that can be mobilized by Substance P since the body would mobilize these stem cells in response to endogenous signals of pain.

The present disclosure provides the use of an antibody to the NK-1R to select out and expand this population of mesenchymal stem cells to therapeutic dosages, effectively enabling a therapeutic strategy utilizing the mesenchymal stem cells and mesenchymal precursor cells that the body would normally release in response to pain.

In some aspects, the present disclosure provides compositions comprising adult bone marrow derived precursors of mesenchymal stem cells. These cells can be administered in vivo, such as for example, to treat heart disease, diabetes, stroke, pain, aging, and inflammatory and autoimmune diseases such as lupus, inflammatory bowel diseases, arthritis, osteoarthritis, graft versus host disease, and allogenic organ rejection.

In some aspects, the present disclosure provides a method of preventing or treating cardiovascular diseases or disorders comprising isolating NK1R+ mesenchymal stem cell precursors (MSCs) from bone marrow of a subject; administering to a patient a therapeutically effective amount of isolated NK1R+ mesenchymal stem cell (MSC) precursors.

In one embodiment, the NK1R+ MSCs are isolated from bone marrow cells which express the NK1 receptor. The NK1R+ stem cells are isolated from donors (or sources) comprising: autologous, syngeneic, allogeneic, or xenogeneic. The MSC precursor cells can differentiate into at least one lineage comprising: myocardial, vascular, or endothelial lineages.

In another embodiment, the isolated precursor mesenchymal stem cells are cultured ex vivo and expanded prior to administration to a patient. In one embodiment, the adherent stem cells are expanded and administered to a patient. In another embodiment, the precursor mesenchymal stem cells are optionally administered to a patient in varying concentrations over a period of time. In one embodiment, the precursor mesenchymal stem cells are optionally conditioned with media conditioned by heart derived stromal cells. In one embodiment. the precursor mesenchymal stem cells are optionally conditioned with media containing substance P.

In another embodiment, the exosomes, extracellular vesicles and/or micro RNAs are derived from the NK-1R+ cells.

In another embodiment, one or more agents are optionally administered to the patient, the agents comprising at least one of: cytokines, chemotactic factors, growth factors, or differentiation factors.

In some embodiments, an adult stem cell comprises a bone marrow mesenchymal stem cell (MSC) precursor derived cell having a NK1R+ phenotype.

In some embodiments, the therapeutic developed from allogenic NK1R+ Mesenchymal cells is tissue matched to the recipient.

In some embodiments, the mesenchymal precursor cells are cultured in animal serum free media. In some embodiments, the mesenchymal precursor cells are cultured in serum free media.

In some embodiments, the culture expanded NK1R+ cells are delivered in a biopolymer matrix.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
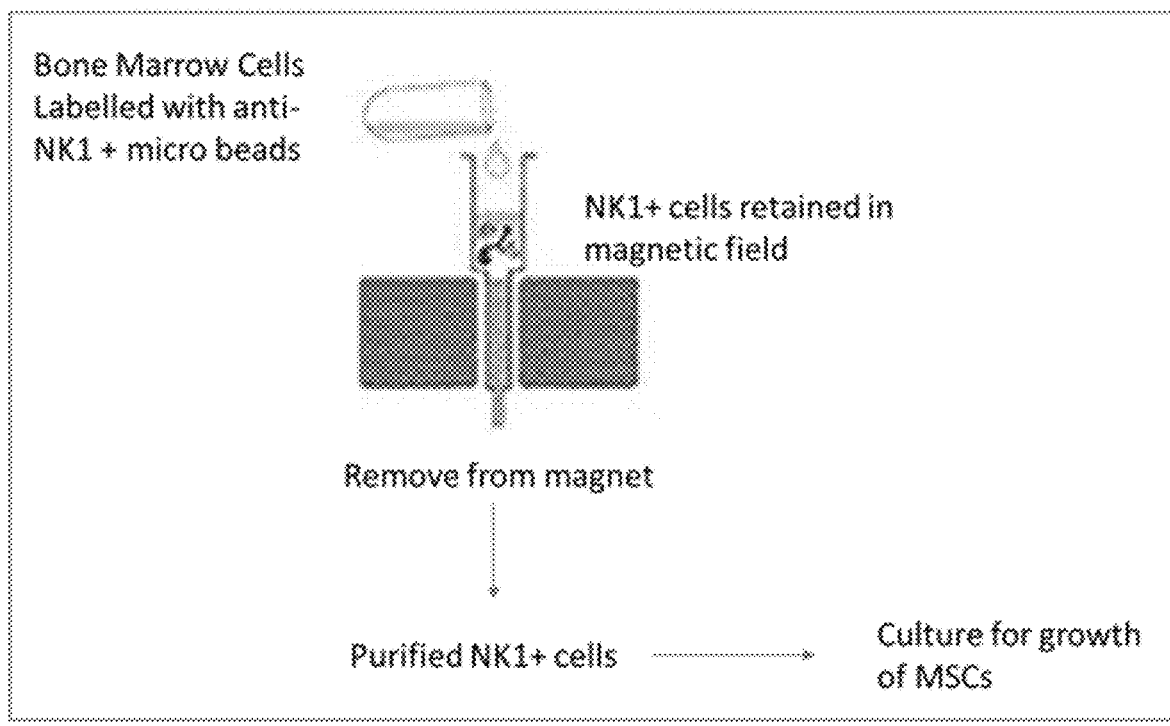
FIG. 1 shows the process of selecting purified NK1R+ cells.
Figure 2:
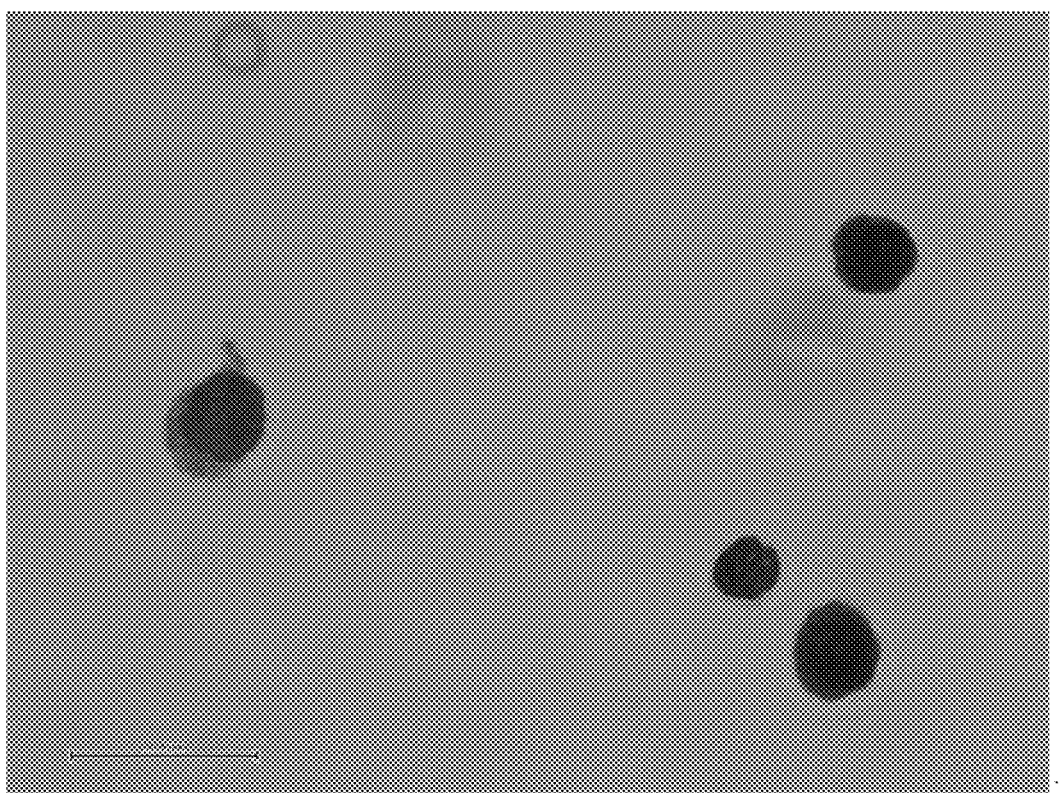
FIG. 2 shows the morphology of NK1R+ cells. Cytospins were prepared and stained with Wright Giemsa. The NK-1R+ cells have a primitive morphology with a low cytoplasm to nucleus ratio.
Figure 3:
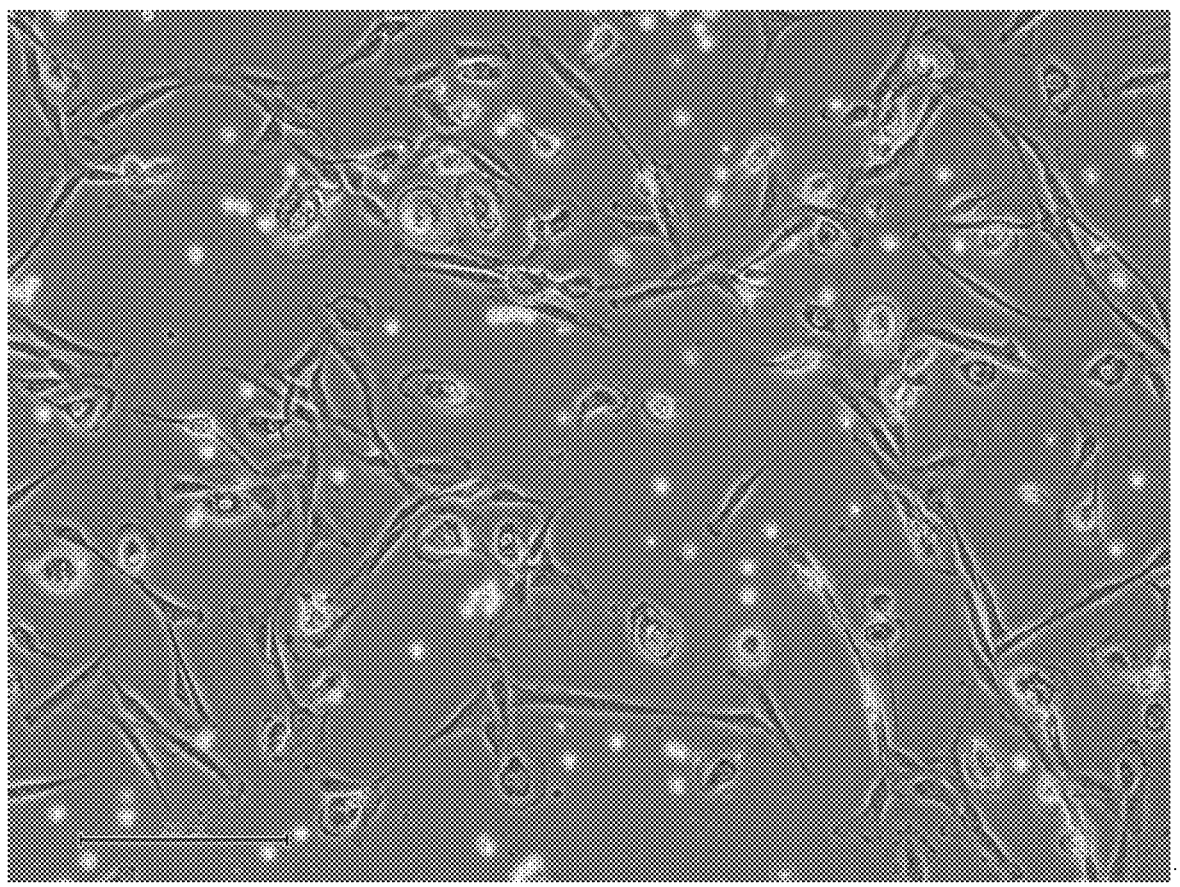
FIG. 3 shows mesenchymal stem cell (MSC) formation from NK1R+ cells at 2 weeks of culture.
Figure 4:
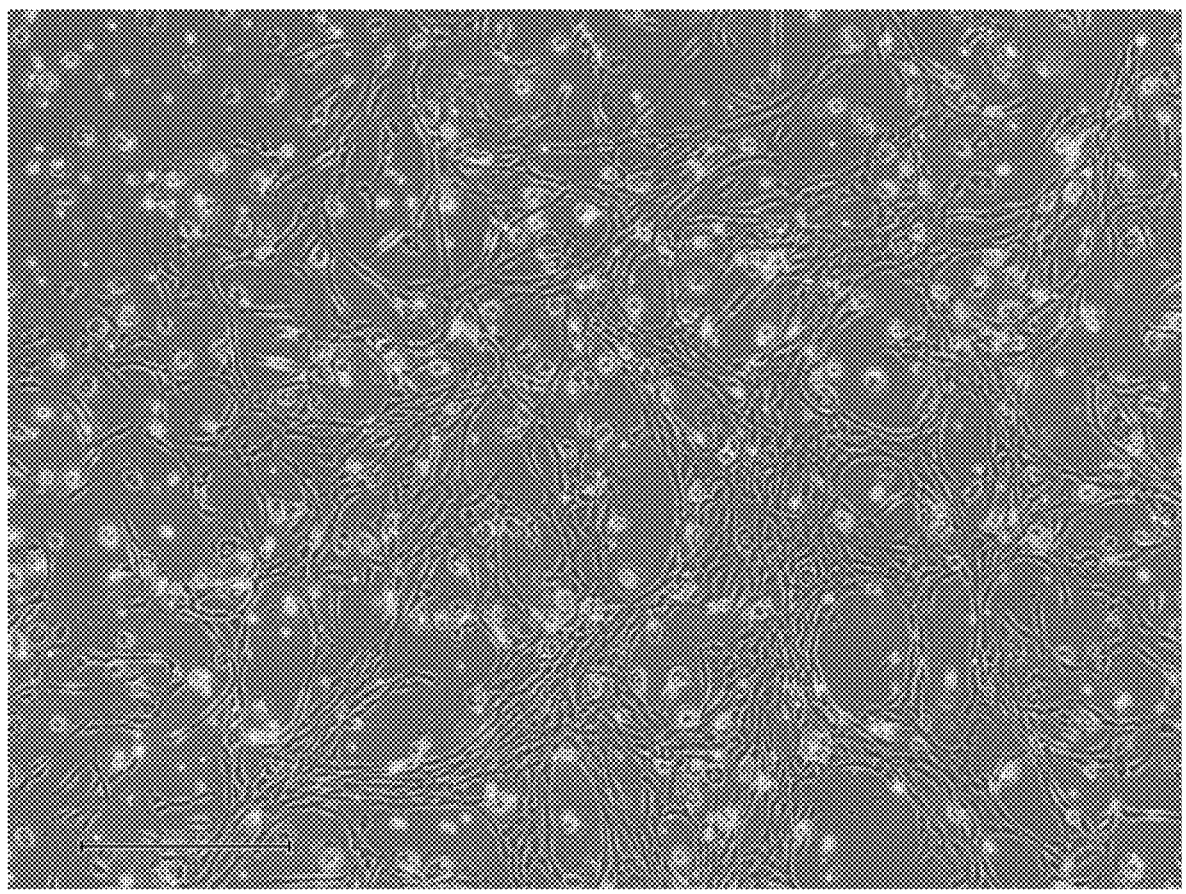
FIG. 4 shows mesenchymal stem cell (MSC) formation from NK1R+ cells at 3 weeks of culture.
Figure 5:
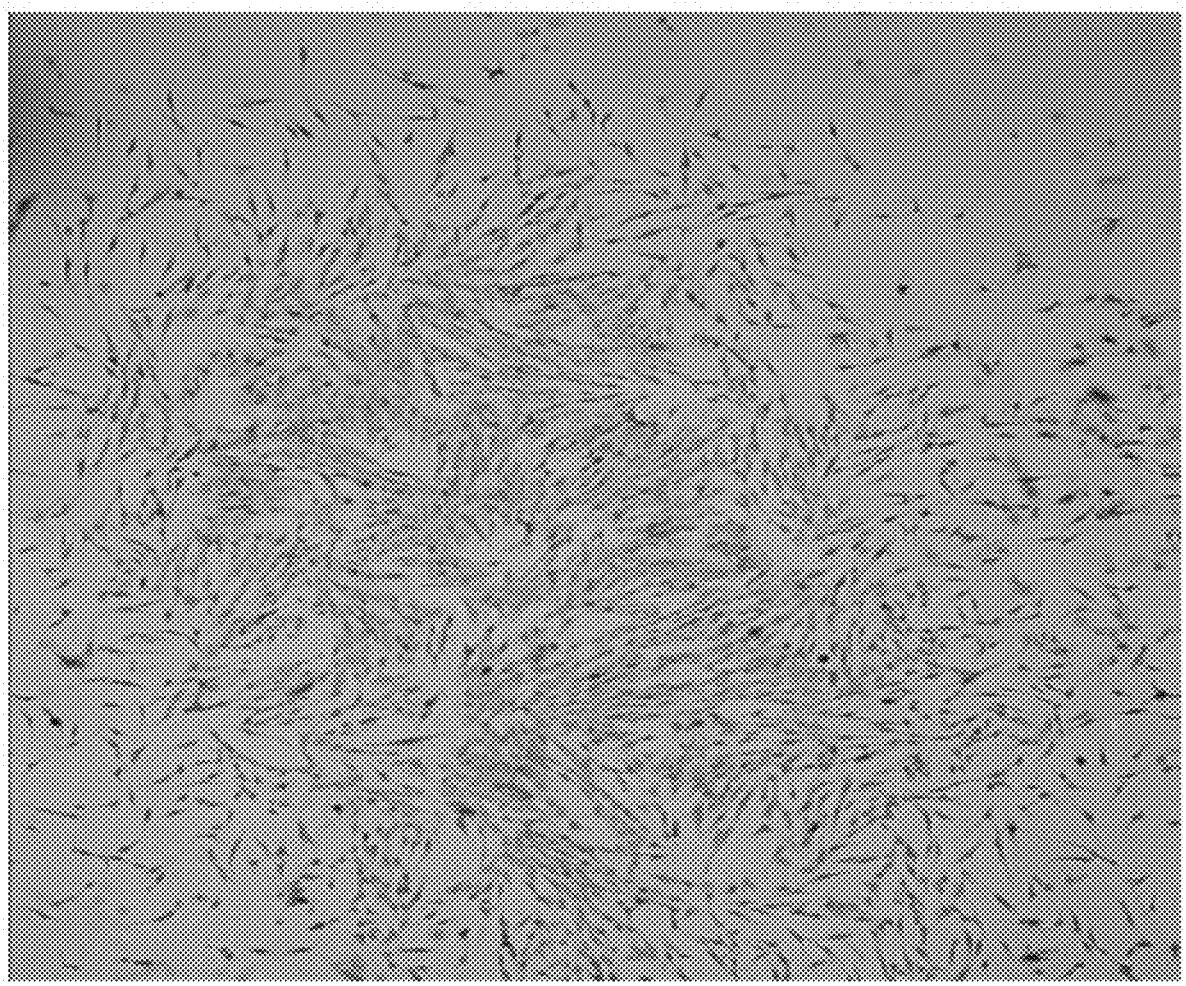
FIG. 5 shows a typical Colony Forming Unit Fibroblast (CFU-F) colony at day 10 of culture.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Embodiments of the invention may be practiced without the theoretical aspects presented. Moreover, the theoretical aspects are presented with the understanding that Applicants do not seek to be bound by the theory presented.

Definitions

Unless defined otherwise, all technical and scientific terms used herein have the same meaning as is commonly understood by one of skill in the art to which this invention belongs. All patents and publications referred to herein are incorporated by reference.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

A "stem cell" can refer to an undifferentiated cell which is capable of essentially unlimited propagation either in vivo or ex vivo and capable of differentiation to other cell types. This can be to certain differentiated, committed, immature, progenitor, or mature cell types present in the tissue from which it was isolated, or dramatically differentiated cell types, such as for example the erythrocytes and lymphocytes that derive from a common precursor cell, or even to cell types at any stage in a tissue completely different from the tissue from which the stem cell is obtained. For example, blood stem cells may become brain cells or liver cells, neural stem cells can become blood cells, such that stem cells are pluripotential, and given the appropriate signals from their environment, they can differentiate into any tissue in the body.

"Propagation," "propagating," or "propagated" can be determined, for example, by the ability of an isolated stem cell to be cultivated through at least 50, preferably 100, and even up to 200 or more cell divisions in a cell culture system. Stem cells can be "totipotent," meaning that they can give rise to all the cells of an organism as for germ cells. Stem cells can also be "pluripotent," meaning that they can give rise to many different cell types, but not all the cells of an organism. When a stem cell differentiates it generally gives rise to a more adult cell type, which may be a partially differentiated cell such as a progenitor cell, a differentiated cell, or a terminally differentiated cell. Stem cells can be highly motile.

"Isolating a stem cell" can refer to the process of removing a stem cell from a tissue sample and separating away other cells which are not stem cells of the tissue. An isolated stem cell can be generally free from contamination by other cell types, i.e. "homogeneity" or purity" and can generally have the capability of propagation and differentiation to produce mature cells of the tissue from which it was isolated. An isolated stem cell can exist in the presence of a small fraction of other cell types which do not interfere with the utilization of the stem cell for analysis or production of other, differentiated cell types. Isolated stem cells will generally be at least 30%, 40%, 50%, 60%, 70%, 80%, 85%, 90%, 95%, 98%, 99%, or 99.9% pure. Preferably, isolated stem cells according to the invention will be at least 98% or at least 99% pure.

As used herein, "culturing" can refer to propagating or nurturing a cell, collection of cells, tissue, or organ, by incubating for a period of time in an environment and under conditions which support cell viability or propagation. Culturing can include one or more of the steps of expanding and proliferating a cell, collection of cells, tissue, or organ according to the invention.

"Bone marrow derived progenitor cell" (BMDC) or "bone marrow derived stem cell" can refer to a primitive stem cell with the machinery for self-renewal constitutively active. Bone marrow derived progenitor cell" (BMDC) or "bone marrow derived stem cell" can include stem cells that are totipotent, pluripotent and precursors.

A "precursor cell" can be any cell in a cell differentiation pathway that is capable of differentiating into a more mature cell.

The term "precursor cell population" can refer to a group of cells capable of developing into a more mature cell. A precursor cell population can comprise cells that are totipotent, cells that are pluripotent and cells that are stem cell lineage restricted (such as cells capable of developing into less than all hematopoietic lineages, or into, for example, only cells of erythroid lineage).

As used herein, the term "autologous" can refer to any material derived from the same individual to whom it is later to be re-introduced into the individual.

The term "xenogeneic cell" can refer to a cell that derives from a different animal species than the animal species that becomes the recipient animal host in a transplantation or vaccination procedure.

The term "allogeneic cell" can refer to a cell that is of the same animal species but genetically different in one or more genetic loci as the animal that becomes the "recipient host". This can apply to cells transplanted from one animal to another non-identical animal of the same species.

The term "syngeneic cell" can refer to a cell that is of the same animal species and has the same genetic composition for most genotypic and phenotypic markers as the animal who becomes the recipient host of that cell line in a transplantation or vaccination procedure. This can apply to cells transplanted from identical twins or can be applied to cells transplanted between highly inbred animals.

As used herein, the term "safe and effective amount" or "therapeutic amount" can refer to the quantity of a component that is sufficient to yield a desired therapeutic response without undue adverse side effects (such as toxicity, irritation, or allergic response) commensurate with a reasonable benefit/risk ratio when used in the manner of this invention.

As defined herein, "a therapeutically effective amount" of an agent or compound, cells etc., (i.e., an effective dosage) can mean an amount sufficient to produce a therapeutically (e.g., clinically) desirable result. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds of the invention can include a single treatment or a series of treatments. A "prophylactically effective amount" may refer to the amount of precursor mesenchymal stem cells sufficient to prevent the recurrence of heart diseases or disorders, for example, ischemia, or the occurrence of such in a patient, including but not limited to those predisposed to heart disease, for example those genetically predisposed to heart disease, stroke, etc. A prophylactically effective amount may also refer to the amount of the prophylactic agent that provides a prophylactic benefit in the prevention of disease.

"Patient" or "subject" can refer to mammals and includes human and veterinary subjects.

As used herein the phrase "diagnosing" can refer to classifying a disease or a symptom, determining a severity of the disease, monitoring disease progression, forecasting an outcome of a disease and/or prospects of recovery. The term "detecting" can also optionally encompass any of the above. A "biological sample obtained from the subject" can also optionally comprise a sample that has not been physically removed from the subject.

"Treatment" can be an intervention performed with the intention of preventing the development or altering the pathology or symptoms of a disorder. "Treatment" can refer to both therapeutic treatment and prophylactic or preventative measures. Those in need of treatment can include those already with the disorder as well as those in which the disorder is to be prevented. "Ameliorated" or "treatment" can refer to a symptom that approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests.

The term "sample" can be interpreted in its broadest sense. A "sample" can refer to a biological sample, such as, for example; one or more cells, tissues, or fluids (including, without limitation, plasma, serum, whole blood, cerebrospinal fluid, lymph, tears, urine, saliva, milk, pus, and tissue exudates and secretions) isolated from an individual or from cell culture constituents, as well as samples obtained from, for example, a laboratory procedure. A biological sample can comprise chromosomes isolated from cells (e.g., a spread of metaphase chromosomes), organelles or membranes isolated from cells, whole cells or tissues, nucleic acid such as genomic DNA in solution or bound to a solid support such as for Southern analysis, RNA in solution or bound to a solid support such as for Northern analysis, cDNA in solution or bound to a solid support, oligonucleotides in solution or bound to a solid support, polypeptides or peptides in solution or bound to a solid support, a tissue, a tissue print and the like.

Numerous well known tissue or fluid collection methods can be utilized to collect the biological sample from the subject in order to determine the level of DNA, RNA and/or polypeptide of the variant of interest in the subject. Examples include, but are not limited to, fine needle biopsy, needle biopsy, core needle biopsy and surgical biopsy (e.g., brain biopsy), and lavage. Regardless of the procedure employed, once a biopsy/sample is obtained the level of the variant can be determined and a diagnosis can thus be made.

As used herein, "heart disease or disorders" or "cardiovascular diseases or disorders" can refer to any type of heart disease or disorders including cardiomyopathy, hypertrophic cardiomyopathy, dilated cardiomyopathy, atherosclerosis, coronary artery disease, ischemic heart disease, myocarditis, viral infection, wounds, hypertensive heart disease, valvular disease, congenital heart disease, myocardial infarction, congestive heart failure, arrhythmias, diseases resulting in remodeling of the heart, heart failure, ischemia, myocardial infarction, transplantation, hypertension, restenosis, angina pectoris, rheumatic heart disease, or congenital cardiovascular defects. Diseases or disorders of the heart can be due to any reason, such as for example, damage to cardiac tissue such as a loss of contractility (e.g., as might be demonstrated by a decreased ejection fraction).

Cardiac damage or disorders characterized by insufficient cardiac function includes any impairment or absence of a normal cardiac function or presence of an abnormal cardiac function. Abnormal cardiac function can be the result of disease, injury, and/or aging. As used herein, abnormal cardiac function can include morphological and/or functional abnormality of a cardiomyocyte, a population of cardiomyocytes, or the heart itself. Non-limiting examples of morphological and functional abnormalities include physical deterioration and/or death of cardiomyocytes, abnormal growth patterns of cardiomyocytes, abnormalities in the physical connection between cardiomyocytes, under- or over-production of a substance or substances by cardiomyocytes, failure of cardiomyocytes to produce a substance or substances which they normally produce, and transmission of electrical impulses in abnormal patterns or at abnormal times. Abnormalities at a more gross level include dyskinesis, reduced ejection fraction, changes as observed by echocardiography (e.g., dilatation), changes in EKG, changes in exercise tolerance, reduced capillary perfusion, and changes as observed by angiography. Abnormal cardiac function can be seen with many disorders including, for example, ischemic heart disease, e.g., angina pectoris, myocardial infarction, chronic ischemic heart disease, hypertensive heart disease, pulmonary heart disease (cor pulmonale), valvular heart disease, e.g., rheumatic fever, mitral valve prolapse, calcification of mitral annulus, carcinoid heart disease, infective endocarditis, congenital heart disease, myocardial disease, e.g., myocarditis, dilated cardiomyopathy, hypertensive cardiomyopathy, cardiac disorders which result in congestive heart failure, and tumors of the heart, e.g., primary sarcomas and secondary tumors. Heart damage also can include wounds, such as for example, knife wound; biological (e.g. viral; autoimmune diseases) or chemical (e.g. chemotherapy, drugs); surgery; transplantation and the like.

"Myocardial ischemia" can refer to a lack of oxygen flow to the heart which results in myocardial ischemic damage. As used herein, the phrase "myocardial ischemic damage" can include damage caused by reduced blood flow to the myocardium. Non-limiting examples of causes of myocardial ischemia and myocardial ischemic damage include: decreased aortic diastolic pressure, increased intraventricular pressure and myocardial contraction, coronary artery stenosis (e.g., coronary ligation, fixed coronary stenosis, acute plaque change (e.g., rupture, hemorrhage), coronary artery thrombosis, vasoconstriction), aortic valve stenosis and regurgitation, and increased right atrial pressure. Non-limiting examples of adverse effects of myocardial ischemia and myocardial ischemic damage include: myocyte damage (e.g., myocyte cell loss, myocyte hypertrophy, myocyte cellular hyperplasia), angina (e.g., stable angina, variant angina, unstable angina, sudden cardiac death), myocardial infarction, and congestive heart failure. Damage due to myocardial ischemia can be acute or chronic, and consequences can include scar formation, cardiac remodeling, cardiac hypertrophy, wall thinning, dilatation, and associated functional changes. The existence and etiology of acute or chronic myocardial damage and/or myocardial ischemia can be diagnosed using any of a variety of methods and techniques well known in the art including, e.g., non-invasive imaging (e.g., MRI, echocardiography), angiography, stress testing, assays for cardiac-specific proteins such as cardiac troponin, and clinical symptoms. These methods and techniques as well as other appropriate techniques can be used to determine which subjects are suitable candidates for the treatment methods described herein.

Bone Marrow Derived NK1R+ Cells

Ischemic cardiomyopathy is the leading cause of heart failure in developed countries. Few therapies exist to improve cardiac function once infarct remodeling has occurred, and treatments that actually reverse deleterious remodeling of the heart after a myocardial infarction (MI) are lacking. Administration of adult bone marrow derived progenitor cells into the heart holds promise to regenerate myocardium. Studies have demonstrated in preclinical models and in humans the ability of bone marrow (BM) derived mesenchymal stem cells (MSCs) delivered to the heart via surgical and catheter delivery systems to engraft, support reverse remodeling, improve cardiac function, and reduce scar size. While MSCs have shown great promise, these cells require 4 to 5 weeks of culture to obtain sufficient quantities to be injected. Precursors of MSCs, which can be isolated from the bone marrow based upon expression of the neurokinin 1 receptor (NK1R) and the NK1R+ cells, are a readily available cell source for therapeutic use. Bone marrow derived NK1R+ cells can be obtained from a bone marrow aspiration and isolated to sufficient quantities in about 4 to 5 hours, providing a logistical advantage for immediate use. Moreover, these cells are dramatically superior in efficacy to cultured MSCs. Without wishing to be bound by theory, the central hypothesis is that BM-NK1R++ cells delivered by surgical injection will engraft, improve cardiac function, and reduce scar size.

Cellular therapy for chronic ischemic cardiomyopathy offers the potential to prevent further tissue damage which would lead to heart failure. In some aspects, the present disclosure provides that human NK1R+ cells are precursors of MSC. Adequate numbers of NK1R++ cells can be isolated from BM in about four to five hours providing a major logistic advance to treat patients immediately with autologous bone marrow derived therapy.

In some embodiments, bone marrow derived (BM) derived precursor mesenchymal stem NK1R+ cells are utilized in the treatment of ischemic tissue in patients with heart failure.

In some embodiments, a method of preventing or treating cardiovascular diseases or disorders comprises administering to a patient an effective amount of NK1R+ stem cells. The NK1R+ cells can be isolated from bone marrow cells expressing the neurokinin 1 receptor.

In some embodiments, the NK1R+ stem cells are autologous, syngeneic, allogeneic, xenogeneic or combinations thereof. The administered stem cells can populate and repair damaged tissue, for example, cardiac tissue. These cells can differentiate into the various lineages resulting in the regeneration and repair of damaged tissue.

In some embodiments, one or more agents are administered to the patient, the agents comprising at least one of: cytokines, chemotactic factors, growth factors, or differentiation factors.

In some embodiments, the methods for treating a patient with a heart disease or injury comprises administering a therapeutic cell composition to a patient with a disease or injury of the heart or circulatory system, and evaluating the patient for improvements in cardiac function, wherein said cell composition comprises NK1R+ as described herein. In one embodiment, the heart disease is a cardiomyopathy. In some embodiments, the cardiomyopathy is either idiopathic or a cardiomyopathy with a known cause. In other embodiments, the cardiomyopathy is either ischemic or nonischemic in nature. In another embodiments, the disease of the heart or circulatory system comprises one or more of angioplasty, aneurysm, angina (angina pectoris), aortic stenosis, aortitis, arrhythmias, arteriosclerosis, arteritis, asymmetric septal hypertrophy (ASH), atherosclerosis, atrial fibrillation and flutter, bacterial endocarditis, Barlow's Syndrome (mitral valve prolapse), bradycardia, Buerger's Disease (thromboangiitis obliterans), cardiomegaly, cardiomyopathy, carditis, carotid artery disease, coarctation of the aorta, congenital heart diseases (congenital heart defects), congestive heart failure (heart failure), coronary artery disease, Eisenmenger's Syndrome, embolism, endocarditis, erythromelalgia, fibrillation, fibromuscular dysplasia, heart block, heart murmur, hypertension, hypotension, idiopathic infantile arterial calcification, Kawasaki Disease (mucocutaneous lymph node syndrome, mucocutaneous lymph node disease, infantile polyarteritis), metabolic syndrome, microvascular angina, myocardial infarction (heart attacks), myocarditis, paroxysmal atrial tachycardia (PAT), periarteritis nodosa (polyarteritis, polyarteritis nodosa), pericarditis, peripheral vascular disease, critical limb ischemia, diabetic vasculopathy, phlebitis, pulmonary valve stenosis (pulmonic stenosis), Raynaud's Disease, renal artery stenosis, renovascular hypertension, rheumatic heart disease, septal defects, silent ischemia, syndrome X, tachycardia, Takayasu's Arteritis, Tetralogy of Fallot, transposition of the great vessels, tricuspid atresia, truncus arteriosus, valvular heart disease, varicose ulcers, varicose veins, vasculitis, ventricular septal defect, Wolff-Parkinson-White Syndrome, or endocardial cushion defect.

In some embodiments, the disease of the heart or circulatory system comprises one or more of acute rheumatic fever, acute rheumatic pericarditis, acute rheumatic endocarditis, acute rheumatic myocarditis, chronic rheumatic heart diseases, diseases of the mitral valve, mitral stenosis, rheumatic mitral insufficiency, diseases of aortic valve, diseases of other endocardial structures, ischemic heart disease (acute and subacute), angina pectoris, diseases of pulmonary circulation (acute pulmonary heart disease, pulmonary embolism, chronic pulmonary heart disease), kyphoscoliotic heart disease, myocarditis, endocarditis, endomyocardial fibrosis, endocardial fibroelastosis, atrioventricular block, cardiac dysrhythmias, myocardial degeneration, diseases of the circulatory system including cerebrovascular disease, occlusion and stenosis of precerebral arteries, occlusion of cerebral arteries, diseases of arteries, arterioles and capillaries (atherosclerosis, aneurysm), or diseases of veins and lymphatic vessels.

In some embodiments, treatment comprises treatment of a patient with a cardiomyopathy with a therapeutic cell composition comprising NK1R+ cells, either with or without another cell type. In other embodiments, the patient experiences benefits from the therapy, for example from the ability of the cells to support the growth of other cells, including stem cells or progenitor cells present in the heart, from the tissue ingrowth or vascularization of the tissue, and from the presence of beneficial cellular factors, chemokines, cytokines and the like.

Improvement in an individual having a disease or disorder of the circulatory system, wherein the individual is administered the NK1R+ cells or therapeutic compositions provided herein, can be assessed or demonstrated by detectable improvement in one or more symptoms of the disease or disorder of the circulatory system.

In some embodiments, improvement in an individual having a disease or disorder of the circulatory system, wherein the individual is administered the NK1R+ cells or therapeutic compositions provided herein, can be assessed or demonstrated by detectable improvement in one or more, indicia of cardiac function, for example, demonstration of detectable improvement in one or more of chest cardiac output (CO), cardiac index (CI), pulmonary artery wedge pressures (PAWP), and cardiac index (CI), % fractional shortening (% FS), ejection fraction (EF), left ventricular ejection fraction (LVEF); left ventricular end diastolic diameter (LVEDD), left ventricular end systolic diameter (LVESD), contractility (e.g. dP/dt), pressure-volume loops, measurements of cardiac work, an increase in atrial or ventricular functioning; an increase in pumping efficiency, a decrease in the rate of loss of pumping efficiency, a decrease in loss of hemodynamic functioning; and a decrease in complications associated with cardiomyopathy, as compared to the individual prior to administration of NK1R+ cells.

Improvement in an individual receiving the therapeutic compositions provided herein can be assessed by subjective metrics, e.g., the individual's self-assessment about his or her state of health following administration.

In certain embodiments, the methods of treatment provided herein comprise inducing the therapeutic NK1R+ cells to differentiate along mesenchymal lineage, e.g., towards a cardiomyogenic, angiogenic or vasculogenic phenotype, or into cells such as myocytes, cardiomyocytes, endothelial cells, myocardial cells, epicardial cells, vascular endothelial cells, smooth muscle cells (e.g. vascular smooth muscle cells).

Administration of NK1R+ cells, or therapeutic compositions comprising such cells, to an individual in need thereof, can be accomplished, e.g., by transplantation, implantation (e.g., of the cells themselves or the cells as part of a matrix-cell combination), injection (e.g., directly to the site of the disease or condition, for example, directly to an ischemic site in the heart of an individual who has had a myocardial infarction), infusion, delivery via catheter, or any other means known in the art for providing cell therapy.

In some embodiments, the therapeutic cell compositions are provided to an individual in need thereof, for example, by injection into one or more sites in the individual. In some embodiments, the therapeutic cell compositions are provided by intracardiac injection, e.g., to an ischemic area in the heart. In other embodiments, the cells are injected onto the surface of the heart, into an adjacent area, or even to a more remote area. In some embodiments, the cells can hone to the diseased or injured area.

An individual having a disease or condition of the coronary or vascular systems can be administered NK1R+ cells at any time the cells would be therapeutically beneficial. In certain embodiments, for example, the cells or therapeutic compositions of the invention are administered within 1, 2, 3, 4, 5, 6, 7, 8, 9, 10, 11, 12, 13, 14, 15, 16, 17, 18, 19, 20, 21, 22, 23, or 24 hours, or 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days of the myocardial infarction. Administration proximal in time to a myocardial infarction, e.g., within 1-3 or 1-7 days, is preferable to administration distal in time, e.g., after 3 or 7 days after a myocardial infarction. In other embodiments, the cells or therapeutic compositions of the invention are administered within 1, 2, 3, 4, 5, 6, 7, 8, 9, 10, 11, 12, 13, 14, 15, 16, 17, 18, 19, 20, 21, 22, 23, or 24 hours, or 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days of initial diagnosis of the disease or condition.

Also provided herein are kits for use in the treatment of myocardial infarction. The kits provide the therapeutic cell composition and an applicator, along with instructions for use. The therapeutic cell composition can be prepared in a pharmaceutically acceptable form, for example by mixing with a pharmaceutically acceptable carrier, The kit can be used in the field, for example in a physician's office, or by an emergency care provider to be applied to a patient diagnosed as having had a myocardial infarction or similar cardiac event.

In some aspects of the methods of treatment provided herein, the NK1R+ cells are administered with stem cells that are not NK1R+ cells, myoblasts, myocytes, cardiomyoblasts, cardiomyocytes, or progenitors of myoblasts, myocytes, cardiomyoblasts, and/or cardiomyocytes.

In some embodiments, the methods of treatment provided herein comprise administering NK1R+ cells, e.g., a therapeutic composition comprising the cells, to a patient with a disease of the heart or circulatory system; and evaluating the patient for improvements in cardiac function, wherein the therapeutic cell composition is administered as a matrix-cell complex. In certain embodiments, the matrix is a scaffold, preferably bioabsorbable, comprising at least the cells.

In some embodiments, populations of NK1R+ cells are incubated or are administered to a patient in the presence of one or more factors which stimulate stem or progenitor cell differentiation along a cardiogenic, angiogenic, hemangiogenic, or vasculogenic pathway. Such factors are known in the art; determination of suitable conditions for differentiation can be accomplished with routine experimentation. Such factors can include, but are not limited to factors, such as growth factors, chemokines, cytokines, cellular products, demethylating agents, and other stimuli that are now known or later determined to stimulate differentiation, for example of stem cells, along cardiogenic, angiogenic, hemangiogenic, or vasculogenic pathways or lineages. For example, NK1R++ cells may be differentiated along cardiogenic, angiogenic, hemangiogenic, or vasculogenic pathways or lineages by culture of the cells in the presence of factors comprising at least one of a demethylation agent, a BMP, FGF, Wnt factor protein, Hedgehog, and/or anti-Wnt factors.

Inclusion of demethylation agents tends to allow the cells to differentiate along mesenchymal lines, toward a cardiomyogenic pathway. Differentiation can be determined by, for example, expression of at least one of cardiomyosin, skeletal myosin, or GATA4; or by the acquisition of a beating rhythm, spontaneous or otherwise induced; or by the ability to integrate at least partially into a patient's cardiac muscle without inducing arrhythmias. Demethylation agents that can be used to initiate such differentiation include, but are not limited to, 5-azacytidine, 5-aza-2'-deoxycytidine, dimethylsulfoxide, chelerythrine chloride, retinoic acid or salts thereof, 2-amino-4-(ethylthio)butyric acid, procainamide, and procaine.

In certain embodiments herein, cells become cardiomyogenic, angiogenic, hemangiogenic, or vasculogenic cells, or progenitors. Cells can integrate into a recipient's cardiovascular system, including but not limited to heart muscle, vascular and other structures of the heart, cardiac or peripheral blood vessels, and the like. In other embodiments, the NK1R++ cells differentiate into cells acquiring two or more of the indicia of cardiomyogenic cells or their progenitors, and able to integrate into a recipient's heart or vasculature. In specific embodiments, the cells, which administered to an individual, result in no increase in arrhythmias, heart defects, blood vessel defects or other anomalies of the individual's circulatory system or health. In certain embodiments, the NK1R++ cells act to promote the differentiation of stem cells naturally present in the patient's cardiac muscle, blood vessels, blood and the like to themselves differentiate into for example, cardiomyocytes, or at least along cardiomyogenic, angiogenic, hemangiogenic, or vasculogenic lines.

NK1R++ cells, and populations of such cells, can be provided therapeutically or prophylactically to an individual, e.g., an individual having a disease, disorder or condition of, or affecting, the heart or circulatory system. Such diseases, disorders or conditions can include congestive heart failure due to atherosclerosis, cardiomyopathy, or cardiac injury, e.g., an ischemic injury, such as from myocardial infarction or wound (acute or chronic).

The NK1R++ cells can be administered to an individual in the form of a therapeutic composition comprising the cells and another therapeutic agent, such as insulin-like growth factor (IGF), platelet-derived growth factor (PDGF), epidermal growth factor (EGF), fibroblast growth factor (FGF), vascular endothelial growth factor (VEGF), hepatocyte growth factor (HGF), IL-8, an antithrombogenic agent (e.g., heparin, heparin derivatives, urokinase, and PPack (dextrophenylalanine proline arginine chloromethylketone); antithrombin compounds, platelet receptor antagonists, antithrombin antibodies, anti-platelet receptor antibodies, aspirin, dipyridamole, protamine, hirudin, prostaglandin inhibitors, and/or platelet inhibitors), an antiapoptotic agent (e.g., EPO, EPO derivatives and analogs, and their salts, TPO, IGF-I, IGF-II, hepatocyte growth factor (HGF), or caspase inhibitors), an anti-inflammatory agent (e.g., P38 MAP kinase inhibitors, statins, IL-6 and IL-1 inhibitors, Pemirolast, Tranilast, Remicade, Sirolimus, nonsteroidal anti-inflammatory compounds, for example, acetylsalicylic acid, ibuprofen, Tepoxalin, Tolmetin, or Suprofen), an immunosuppressive or immunomodulatory agent (e.g., calcineurin inhibitors, for example cyclosporine, Tacrolimus, mTOR inhibitors such as Sirolimus or Everolimus; antiproliferatives such as azathioprine and mycophenolate mofetil; corticosteroids, e.g., prednisolone or hydrocortisone; antibodies such as monoclonal anti-IL-2Rα receptor antibodies, Basiliximab, Dacliziuma, polyclonal anti-T-cell antibodies such as anti-thymocyte globulin (ATG), anti-lymphocyte globulin (ALG), and the monoclonal anti-T cell antibody OKT3, and/or an antioxidant (e.g., probucol; vitamins A, C, and E, coenzyme Q-10, glutathione, L cysteine, N-acetylcysteine, or antioxidant derivative, analogs or salts of the foregoing). In certain embodiments, therapeutic compositions comprising the NK1R++ cells further comprise one or more additional cell types, e.g., adult cells (for example, fibroblasts or endodermal cells), or stem or progenitor cells. Such therapeutic agents and/or one or more additional cells can be administered to an individual in need thereof individually or in combinations or two or more such compounds or agents.

In certain embodiments, the individual to be treated is a mammal. In a specific embodiment the individual to be treated is a human. In specific embodiments, the individual is a livestock animal or a domestic animal. In other specific embodiments, the individual to be treated is a horse, sheep, cow or steer, pig, dog or cat.

In some embodiments, the population of stem cells is at least about 80% pure as compared to a control sample of cells isolated from a heart tissue, for example, the stem cell population is about 90% pure as compared to a control sample of cells, for example, the stem cell population is about 95%, 96%, 97%, 98%, 99%, 99.9% pure as compared to a control sample of cells.

In some embodiments, the isolated NK1R+ stem cell populations can be used in any assay desired by the end user, such as for example, expressing a non-native or foreign molecule, a native molecule which may or may not be activated in the cells. Examples of such molecules can be growth factors, receptors, ligands, therapeutic agents, etc. The molecules can be selected by the end user for expression by the isolated stem cells depending on the end user's need. The molecules can comprise, for example, a polypeptide, a peptide, an oligonucleotide, a polynucleotide, an organic or inorganic molecule.

In some embodiments, stem cells can be embryonic stem cells, adult stem cells, umbilical cord blood stem cells, somatic stem cells or cancer stem cells. In preferred embodiments, the stem cells are adult stem cells, preferably cardiac stem cells.

Additionally, the stem cells of the current invention can be hematopoietic stem cells, or mesenchymal stem cells. The stem cells of the current invention can be totipotent, pluripotent, multipotent or unipotent stem cells. Stem cells according to the current invention can be selected for by the presence of one or more stem cell markers including but not limited to: CD133, CD34, CD38, CD117/c-kit, OCT3/4, Nanog, RUNX2, SOX9, Integrin, SPARC, osteocalcin, endoglin and STRO-1.

The stem cells of the current invention can be primary stem cells or can be derived from an established stem cell line, premalignant stem cell line, cancer cell line, or any cell line that manifests any stem cell marker. Primary stem cells can be derived from a cancer patient or a healthy patient.

Administration: Isolation of NK1R+ stem cell populations is useful in many types of applications, for example, transplantation into heart or other organs for the treatment of cardiac diseases or disorders, such as damaged myocardium. As used herein "damaged myocardium" refers to myocardial cells which have been exposed to ischemic conditions. These ischemic conditions may be caused by a myocardial infarction, or other cardiovascular disease or related complaint. The lack of oxygen causes the death of the cells in the surrounding area, leaving an infarct, which will eventually scar. As used herein "age-related cardiomyopathy" refers to the deterioration of the myocardium as a result of intrinsic mechanisms occurring as the organism ages.

In some embodiments, the stem cells are used in methods of repairing and/or regenerating damaged myocardium or age-related cardiomyopathy in a subject in need thereof by administering isolated stem cells to areas of damaged myocardium, wherein the administered stem cells differentiate into one or more of myocytes, endothelial cells, or smooth muscle cells. The differentiated cells can proliferate and form various cardiac structures including coronary arteries, arterioles, capillaries, and myocardium, which are all structures essential for proper function in the heart. The ability to restore both functional and structural integrity is yet another aspect of this disclosure. In some embodiments, the stem cells are adult cardiac stem cells. In another embodiment, adult cardiac stem cells are isolated from cardiac tissue harvested from the subject in need of therapeutic treatment for one of the cardiac or vasculature conditions and implanted back into the subject.

In some embodiments, the isolated NK1R+ stem cells are cultured and expanded ex vivo prior to administration of the stem cells to a patient. The cells can be for example, autologous, syngeneic, allogeneic, xenogeneic or any combination thereof. The same source of stem cells does not have to be used if successive administrations are required.

In some aspects, the present disclosure provides administering a therapeutically effective dose or amount of stem cells to the heart. An effective dose is an amount sufficient to effect a beneficial or desired clinical result. The dose could be administered in one or more administrations. The precise determination of what would be considered an effective dose may be based on factors individual to each patient, including their size, age, area of myocardial damage, and amount of time since damage. One skilled in the art, specifically a physician or cardiologist, would be able to determine the number of stem cells that would constitute an effective dose without undue experimentation.

In some embodiments, the isolated stem cells are activated prior to administration to a subject. Activation of the stem cells can be accomplished by exposing the isolated stem cells to one or more cytokines, such as hepatocyte growth factor (HGF), insulin-like growth factor-1 (IGF-1), or variant thereof. HGF positively influences stem cell migration and homing through the activation of the c-Met receptor (Kollet et al. (2003) *J. Clin. Invest.* 112: 160-169; Linke et al. (2005) *Proc. Natl. Acad. Sci. USA* 102: 8966-8971; Rosu-Myles et al. (2005) *J. Cell. Sci.* 118: 4343-4352; Urbanek et al. (2005) *Circ. Res.* 97: 663-673). Similarly, IGF-1 and its corresponding receptor (IGF-1R) induce cardiac stem cell division, upregulate telomerase activity, hinder replicative senescence and preserve the pool of functionally-competent cardiac stem cells in the heart (Kajstura et al. (2001) *Diabetes* 50: 1414-1424; Torella et al. (2004) *Circ. Res.* 94: 514-524; Davis et al. (2006) *Proc. Natl. Acad. Sci. USA* 103: 8155-8160). In a preferred embodiment, the isolated stem cells are contacted with hepatocyte growth factor (HGF) and/or insulin-like growth factor-1 (IGF-1).

Some other non-limiting examples of cytokines that are suitable for the activation of the isolated stem cells include Activin A, Bone Morphogenic Protein 2, Bone Morphogenic Protein 4, Bone Morphogenic Protein 6, Cardiotrophin-1, Fibroblast Growth Factor 1, Fibroblast Growth Factor 4, Flt3 Ligand, Glial-Derived Neurotrophic Factor, Heparin, Insulin-like Growth Factor-II, Insulin-Like Growth Factor Binding Protein-3, Insulin-Like Growth Factor Binding Protein-5, Interleukin-3, Interleukin-6, Interleukin-8, Leukemia Inhibitory Factor, Midkine, Platelet-Derived Growth Factor AA, Platelet-Derived Growth Factor BB, Progesterone, Putrescine, Stem Cell Factor, Stromal-Derived Factor-1, Thrombopoietin, Transforming Growth Factor-α, Transforming Growth Factor-01, Transforming Growth Factor-P2, Transforming Growth Factor-β3, Vascular Endothelial Growth Factor, Wnt1, Wnt3a, and Wnt5a, as described in Kanemura et al. (2005) Cell Transplant. 14:673-682; Kaplan et al. (2005) Nature 438:750-751; Xu et al. (2005) Methods Mol. Med. 121:189-202; Quinn et al. (2005) Methods Mol. Med. 121:125-148; Almeida et al. (2005) J Biol. Chem. 280:41342-41351; Bamabe-Heider et at (2005) Neuron 48:253-265; Madlambayan et al. (2005) Exp Hematol 33: 1229-1239; Kamanga-Sollo et al. (2005) Exp Cell Res 311:167-176; Heese et al. (2005) Neuro-oncol. 7:476-484; He et al. (2005) Am J. Physiol. 289:H968-H972; Beattie et al. (2005) Stem Cells 23:489-495; Sekiya et al. (2005) Cell Tissue Res 320:269-276; Weidt (2004) Stem Cells 22:890-896; Encabo et at (2004) Stem Cells 22:725-740; and Buytaeri-Hoefen et al. (2004) Stem Cells 22:669-674.

The present disclosure envisions employing functional variants of the above-mentioned cytokines. Functional cytokine variants can retain the ability to bind and activate their corresponding receptors. Variants can include amino acid substitutions, insertions, deletions, alternative splice variants, or fragments of the native protein. For example, neurokinin 1 (NK1) and neurokinin 2 (NK2) are natural splice variants of HGF, which are able to bind to the c-MET receptor. These types of naturally occurring splice variants as well engineered variants of the cytokine proteins that retain function are contemplated by the invention.

In some embodiments, the administration of stem cells to a subject in need thereof is accompanied by the administration of one or more cytokines to the heart. The cytokines can be selected from the group consisting of stem cell factor (SCF), granulocyte-colony stimulating factor (G-CSF), granulocyte-macrophage colony stimulating factor (GM-CSF), stromal cell-derived factor-1, steel factor, vascular endothelial growth factor, macrophage colony stimulating factor, granulocyte-macrophage stimulating factor, hepatocyte growth factor (HGF), insulin-like growth factor-1 (IGF-1), Interleukin-3, or any cytokine capable of the stimulating and/or mobilizing stem cells. In a preferred embodiment, the cytokines are selected from HGF, IGF-1, functional variants of HGF or IGF-1, or combinations thereof. The cytokines can be delivered simultaneously with the NK1R+ population of stem cells. Alternatively, the administration of the cytokines can either precede or follow the administration of the stem cells by a specified time period. The time period may be about 15 minutes, about 30 minutes, about 1 hour, about 3 hours, about 6 hours, about 12 hours, about 24 hours, about 36 hours, about 1 week, about 2 weeks, about 1 month, or about 6 months.

The cytokines can be delivered to the heart by one or more administrations. In one embodiment, cytokines are delivered by a single administration. In another embodiment, multiple administrations of the same dosage of cytokines are delivered to the heart. A preferred embodiment of the invention includes administration of multiple doses of the cytokines to the heart, such that a chemotactic gradient is formed. A chemotactic gradient extending from the atria and/or apex of the heart to the mid-region of the left ventricle may be established by administering multiple doses of increasing cytokine concentration. Alternatively, the chemotactic gradient can be formed from the site of implantation of the stem cells to the mid-region of the left ventricle or the border region of infarcted myocardium.

In one embodiment, at least two cytokines are used in the formation of the chemotactic gradient. In another embodiment, the concentration of the first cytokine remains constant while the concentration of the second cytokine is variable, thereby forming the chemotactic gradient.

In some embodiments, the chemotactic gradient is formed by multiple administrations of IGF-1 and HGF, wherein the concentration of IGF-1 remains constant and the concentration of HGF is variable. In some embodiments, the variable concentrations of HGF may range from about 0.1 to about 400 ng/ml. In other embodiments, the concentration of IGF-1 may be from about 0.1 to about 500 ng/ml.

The isolated NK1R+ population of stem cells and cytokines can be administered to the heart by injection. The injection is preferably intramyocardial. As one skilled in the art would be aware, this is the preferred method of delivery for stem cells and/or cytokines to the heart.

In some embodiments, the stem cells and/or cytokines are administered by injection transendocardially or trans-epicardially. This preferred embodiment allows the cytokines to penetrate the protective surrounding membrane, necessitated by the embodiment in which the cytokines are injected intramyocardially. Some embodiments include the use of a catheter-based approach to deliver the trans-endocardial injection. The use of a catheter precludes more invasive methods of delivery wherein the opening of the chest cavity would be necessitated. As one skilled in the art would appreciate, optimum time of recovery would be allowed by the more minimally invasive procedure. A catheter approach involves the use of such techniques as the BioCardia Helix transendocardial biotherapeutic delivery catheter or similar systems, which can be used to deliver targeted injections or to bathe a targeted area with a therapeutic. Any of the embodiments of the present invention can be administered through the use of such a system to deliver injections or provide a therapeutic. One of skill in the art will recognize alternate systems that also provide the ability to provide targeted treatment through the integration of imaging and a catheter delivery system that can be used with the present invention. Information regarding the use of NOGA and similar systems can be found in, for example, Sherman (2003) Basic Appl. Myol. 13: 11-14; Patel et at (2005) The Journal of Thoracic and Cardiovascular Surgery 130:1631-38; and Perrin et al. (2003) Circulation 107: 2294-2302. In another embodiment, the isolated cardiac stem cells are administered by an intracoronary route of administration. One of skill in the art will recognize other useful methods of delivery or implantation which can be utilized with the present invention, including those described in Dawn et al. (2005) Proc. Natl. Acad. Sci. USA 102, 3766-3771

The methods of the present disclosure are useful for the treatment of cardiovascular disease, including, but not limited to, atherosclerosis, ischemia, hypertension, restenosis, angina pectoris, rheumatic heart disease, congenital cardiovascular defects, age-related cardiomyopathy, and arterial inflammation and other disease of the arteries, arterioles and capillaries. Specifically, the methods of the present invention can provide for the repair and/or regeneration of damaged myocardium resulting from one of the diseases listed above or from the general decline of myocardial cells with age.

In some aspects, the present disclosure provides methods of preventing or treating heart failure in a subject comprising administering an isolated, NK1R+ population of adult cardiac stem cells into the subject's heart and administering an angiotensin II receptor antagonist. In one embodiment, the NK1R+ population adult cardiac stem cells are activated prior to administration by exposure to one or more cytokines as described herein. In another embodiment, one or more cytokines are administered to the heart to form a chemotactic gradient causing the administered adult cardiac stem cells to migrate to areas of myocardial damage. In another embodiment, the one or more cytokines are HGF, IGF-1, or variants thereof. The renin-angiotensin system (RAS) is a hormone system that facilitates the regulation of blood pressure and extracellular volume in the body. When renal perfusion drops, cells in the kidney release the enzyme renin. Renin cleaves angiotensinogen, an inactive precursor peptide secreted by the liver, into angiotensin I. Angiotensin I is subsequently converted into angiotensin II (Ang II) by angiotensin-converting enzyme (ACE), which is predominantly found in the lungs. Ang II produces many effects, including vasoconstriction and secretion of aldosterone and vasopressin, through activation of the AT1 receptor. Ang II has been implicated in the age-dependent accumulation of oxidative damage in the heart (Fiordaliso et al. (2001) *Diabetes* 50: 2363-2375; Kajstura et al. (2001) Diabetes 50: 1414-1424), and has been reported to induce senescence and decrease the number and function of endothelial progenitor cells (Kobayashi et al. (2006) *Hypertens. Res.* 29: 449-455). In addition, Ang II triggers apoptosis in myocytes (Leri et al. (1998) *J. Clin. Invest.* 101: 1326-1342) and may contribute to the progression of heart failure (McMurray et al. (2003) *Lancet* 362: 767-771). In fact, inhibition of AT1 receptors has been shown to improve the clinical outcome of patients with chronic heart failure and prolong life in humans (McMurray et al. (2003) *Lancet* 362: 767-771).

In some aspects, the present disclosure provides methods of preventing heart failure and/or treating chronic heart failure in a subject by administering an Ang II receptor antagonist in combination with administration of adult cardiac stem cells to the subject's heart. In some embodiments, the Ang II receptor antagonist is an antagonist of the AT1 receptor. Some non-limiting examples of Ang II receptor antagonists that would be encompassed by the invention include Valsartan, Telmisartan, Losartan, Irbesartan, Olmesartan, Candesartan, and Eprosartan.

In addition, inhibitors of angiotensin converting enzyme (ACE) can be administered in addition to or instead of the Ang II receptor antagonist. As described above, ACE converts angiotensin I into angiotensin II Inhibition of this enzyme would lead to decreased levels of Ang II and thus reduce the deleterious effects of Ang II on cardiac stem cells. ACE inhibitors which can be used in the methods of the present disclosure include, but are not limited to, Benazepril, Enalapril, Lisinopril, Captopril, Fosinopril, Ramipril, Perindopril, Quinapril, Moexipril, and Trandolapril.

The Ang II receptor antagonists or ACE inhibitors can be administered to the subject in multiple doses subsequent to the administration of the adult cardiac stem cells. The antagonists or inhibitors can be taken on a routine schedule for a set period of time. For example, the inhibitors can be taken once daily for about 1 month, about 2 months, about 3 months, about 6 months, about 12 months, or about 24 months after administration of the adult cardiac stem cells. Other dosing schedules can be employed. One of skill in the art, particularly a physician or cardiologist, would be able to determine the appropriate dose and schedule for the administration of the ACE inhibitors or Ang II receptor antagonists. Preferably, one or more symptoms of heart failure is reduced or alleviated following administration of the cardiac stem cells and the angiotensin II receptor antagonist and/or ACE inhibitor. Symptoms of heart failure include, but are not limited to, fatigue, weakness, rapid or irregular heartbeat, dyspnea, persistent cough or wheezing, edema in the legs and feet, and swelling of the abdomen.

In some embodiments, the present disclosure provides methods for preparing compositions, such as pharmaceutical compositions, including adult stem cells and/or at least one cytokine, for instance, for use in inventive methods for treating cardiovascular disease, heart failure or other cardiac conditions. In one embodiment, the pharmaceutical composition comprises isolated human cardiac stem cells and a pharmaceutically acceptable carrier. In some embodiments, the methods and/or compositions, including pharmaceutical compositions, comprise effective amounts of adult cardiac stem cells or two or more cytokines in combination with an appropriate pharmaceutical agent useful in treating cardiac and/or vascular conditions.

In some embodiments, the pharmaceutical compositions of the present invention are delivered via injection. These routes for administration (delivery) include, but are not limited to, subcutaneous or parenteral including intravenous, intraarterial (e.g. intracoronary), intramuscular, intraperitoneal, intramyocardial, transendocardial, trans-epicardial, intranasal administration as well as intrathecal, and infusion techniques. Accordingly, the pharmaceutical composition can be in a form that is suitable for injection. When administering a therapeutic of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion, and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds. Sterile injectable solutions can be prepared by incorporating the compounds utilized in practicing the present invention in the required amount of the appropriate solvent with various amounts of the other ingredients, as desired.

The pharmaceutical compositions of the present disclosure, e.g., comprising a therapeutic dose of NK1R+ stem cells, can be administered to the subject in an injectable formulation containing any compatible carrier, such as various vehicles, adjuvants, additives, and diluents; or the compounds utilized in the present invention can be administered parenterally to the subject in the form of slow-release subcutaneous implants or targeted delivery systems such as monoclonal antibodies, iontophoretic, polymer matrices, liposomes, and microspheres. The pharmaceutical compositions utilized in the present invention can be administered orally to the subject. Conventional methods such as administering the compounds in tablets, suspensions, solutions, emulsions, capsules, powders, syrups and the like are usable. Known techniques which deliver the compound orally or intravenously and retain the biological activity are preferred.

In one embodiment, a composition of the present invention can be administered initially, and thereafter maintained by further administration. For instance, a composition of the invention can be administered in one type of composition and thereafter further administered in a different or the same type of composition. For example, a composition of the invention can be administered by intravenous injection to bring blood levels to a suitable level. The subject's levels are then maintained by an oral dosage form, although other forms of administration, dependent upon the subject's condition, can be used. The quantity of the pharmaceutical composition to be administered will vary for the subject being treated. In some embodiments, $2\times10^4$ to about $1\times10^5$ adult cardiac stem cells and, optionally, 50-500 µg/kg per day of a cytokine or variant of said cytokine are administered to the subject. The precise determination of what would be considered an effective dose can be based on factors individual to each subject, including their size, age, area of damaged myocardium, and amount of time since damage. Thus, the skilled artisan can readily determine the dosages and the amount of compound and optional additives, vehicles, and/or carrier in compositions to be administered in methods of the invention. Typically, any additives (in addition to the active stem cell(s) and/or cytokine(s)) are present in an amount of 0.001 to 50 wt % solution in phosphate buffered saline, and the active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %. Of course, for any composition to be administered to an animal or human, and for any particular method of administration, it is preferred to determine therefore: toxicity, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. The time for sequential administrations can be ascertained without undue experimentation. Examples of compositions comprising a therapeutic of the invention include liquid preparations for orifice, e.g., oral, nasal, anal, vaginal, peroral, intragastric, mucosal (e.g., perlingual, alveolar, gingival, olfactory or respiratory mucosa) etc., administration such as suspensions, syrups or elixirs; and, preparations for parenteral, subcutaneous, intradermal, intramuscular or intravenous administration (e.g., injectable administration), such as sterile suspensions or emulsions. Such compositions may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Pharmaceutical compositions of the invention are conveniently provided as liquid preparations, e.g., isotonic aqueous solutions, suspensions, emulsions or viscous compositions which may be buffered to a selected pH.

The choice of suitable carriers and other additives will depend on the exact route of administration and the nature of the particular dosage form, e.g., liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form). Solutions, suspensions and gels normally contain a major amount of water (preferably purified water) in addition to the active compound. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors can also be present. The compositions can be isotonic, i.e., they can have the same osmotic pressure as blood and lacrimal fluid. The desired isotonicity of the compositions of this invention can be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions In some embodiments for the methods disclosed herein, intravenous infusion can involve providing allogenic tissue matched cryopreserved NK1R+ cells that have been thawed to provide therapy, washing the cells to reduce the presence of DSMO and infusing the cells through a gravity fed bag in a phosphate buffered saline carrier. Intravenous infusion can be used for, but are not limited to, methods of treating ageing, rheumatoid arthritis, stroke, pulmonary fibrosis, lung cancer and conditions thereof.

In some embodiments for the methods disclosed herein, interstitial delivery can involve providing allogenic tissue matched cryopreserved NK1R+ cells that have been thawed to provide therapy, and then infusing the cells through a penetrating element, such as a needle or catheter guided by XRAY or ULTRASOUND imaging technology directly to the site of injury or disease in a phosphate buffered saline carrier. In some embodiments, interstitial delivery can involve washing the cells to reduce the presence of DSMO, for example prior to infusing the cells. In some embodiments, the NK1R+ cells can be mixed with a suitable biopolymer matrix, such as fibrin sealant or collagen gel, after washing. In some embodiments, interstitial delivery Interstitial delivery can be used for, but are not limited to, methods of treating heart failure, diabetes, liver cirrhosis, degenerative disc disease, osteoarthritis, rheumatoid arthritis, and conditions thereof.

Viscosity of the compositions can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. A pharmaceutically acceptable preservative can be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected. Those skilled in the art will recognize that the components of the compositions should be selected to be chemically inert with respect to the active compound. This will present no problem to those skilled in chemical and pharmaceutical principles, or problems can be readily avoided by reference to standard texts or by simple experiments (not involving undue experimentation), from this disclosure and the documents cited herein.

Compositions can be administered in dosages and by techniques well known to those skilled in the medical and veterinary arts taking into consideration such factors as the age, sex, weight, and condition of the particular subject, and the composition form used for administration (e.g., solid vs. liquid). Dosages for humans or other mammals can be determined without undue experimentation by the skilled artisan, from this disclosure, the documents cited herein, and the knowledge in the art. Suitable regimes for initial administration and further doses or for sequential administrations also are variable, may include an initial administration followed by subsequent administrations; but nonetheless, may be ascertained by the skilled artisan, from this disclosure, the documents cited herein, and the knowledge in the art.

The pharmaceutical compositions of the present invention are used to treat heart failure and cardiovascular diseases, including, but not limited to, atherosclerosis, ischemia, hypertension, restenosis, angina pectoris, rheumatic heart disease, congenital cardiovascular defects and arterial inflammation and other diseases of the arteries, arterioles and capillaries or related complaint. Accordingly, the invention involves the administration of adult stem cells as herein discussed, alone or in combination with one or more cytokines or variant of said cytokine, as herein discussed, for the treatment or prevention of any one or more of these conditions or other conditions involving heart disease or disorders. Advantageous routes of administration involves those best suited for treating these conditions, such as via injection, including, but are not limited to subcutaneous or parenteral including intravenous, intraarterial, intramuscular, intraperitoneal, intramyocardial, transendocardial, transepicardial, intranasal administration as well as intrathecal, and infusion techniques.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Materials and Methods

Non-Standard Abbreviations and Acronyms: Bone Marrow (BM); Colony Forming Unit Fibroblast (CFU-F); Coronary Artery Bypass Grafting (CABG); Ejection Fraction (EF); End Diastolic Volume (EDV); End Systolic Volume (ESV); Mesenchymal Stem Cell (MSC); Mononuclear Cell (MNC); Mouse Heart Stromal Cell Conditioned Media (MsHrtStr CM); Myocardial Infarction (MI); Non adherent MSC (NA-MSC); Recombinant human basic fibroblast growth factor (rhbFGF).

Example 1: Isolation of NK1R+ Cells from Normal Human BM

Bone marrow aspirates were obtained from a patient's iliac crest under conscious sedation and local analgesia by an experienced Hematologist/Oncologist. The BM mononuclear cells were isolated using density gradient centrifugation and then the cells were labeled with microbeads attached to an antibody to NK1R+ and the NK1R+ cells isolated on the CliniMACS clinical device (Miltenyi Biotech, Cologne, Germany). The cells were then washed and prepared for infusion. This process takes approximately 4 to 5 hours.

Example 2: Expansion of MSCs

NK1R+ cells will initially be cultured in 'Complete Media with Antibiotics' consisting of alpha MEM media supplemented with 2 mM L-glutamine, 20% Fetal Bovine Serum (FBS), 100 units/ml penicillin, and 100 ug/ml streptomycin. Subsequent passages will use 'Complete Media without Antibiotics'. The expansion will be performed in flasks using a 37° C., 5% $CO_2$ humidified incubator. The MSCs will be detached from the culture vessels using trypsin exposure.

The NK1R+ cells will be cultured at P0 in 10 flasks and when confluent each flask is passaged to 6×P1 flasks resulting in 60 total flasks. After incubation for approximately one week, the confluent P1 flasks are passaged to P2, this performed over a three day period with 20×P1 flasks passaged on each day to 60×P2 flasks. Each P1 flask is passaged to 3×P2 flasks resulting in 60×P2 flasks each day and 180×P2 flasks total. After further incubation until the MSC are confluent, each set of P2 flasks (ie 60 flasks) are harvested on 3 consecutive days based upon the order of passage at P1 to P2. The harvested allogeneic MSCs are then cryopreserved.

Example 3: Expansion of MSCs

Similar to example 2, NK1R+ cells will initially be cultured in 'Complete Media with Antibiotics' consisting of alpha MEM media supplemented with 2 mM L-glutamine, 20% Fetal Bovine Serum (FBS), 100 units/ml penicillin, and 100 ug/ml streptomycin. Subsequent passages will use 'Complete Media without Antibiotics'. The expansion will be performed in flasks using a 37° C., 5% $CO_2$ humidified incubator. The MSCs will be detached from the culture vessels using trypsin exposure.

The NK1R+ cells will be cultured at P0 in 10 flasks and when confluent each flask's harvested allogeneic MSCs are then cryopreserved such that they may be thawed in expanded in a system such as the Quantum system, a novel hollow fiber bioreactor closed system. NK1R+ cells would be passaged as described above to P1 and the MSCs harvested and cryopreserved in aliquots of 50M MSCs in cryo bags. A typical procedure generates approximately 600M MSCs or 12 bags of 50M. Each bag would be thawed and expanded to P2 on the Quantum system, generating in the range of 600M to 800M MSCs. After expansion on the Quantum system the MSCs are cryopreserved as detailed below.

Example 4: Lot Release Testing of Cells: Final Cell Products Will be Tested for the Following

| Assay | Sample | Acceptance Criteria |
|---|---|---|
| *Sterility: aerobic/anaerobic/fungal | Final Product | Preliminary Result: Negative or No Growth |
| *Sterility: Gram Stain | Thawed Washed Product | No organisms seen (negative) |
| Endotoxin | Thawed Washed Product | Sliding scale based on patient weight. ≤5 EU/kg/hour |
| Viability | Thawed Washed Product | ≥70% |
| #*Mycoplasma*: PCR | Cells in Conditioned Media prior to harvest | Negative by PCR |

Example 5: Cryopreservation and Shipping of Cells to a Clinical Site

MSCs will be suspended in cryoprotectant consisting of Hespan® [6% hetastarch in 0.9% sodium chloride] supplemented with 2% HSA and 5% DMSO). The cells will be aliquoted into cryopreservation bags. After cryopreservation using a control rate freezer, the frozen bags will be placed into the vapor phase nitrogen freezers where they will be stored until issue. QA and the Laboratory Director will review the production records and QC testing results to release the product.

The FINAL PRODUCT and the THAWED WASHED PRODUCT labels will contain the following statement: "CAUTION: New experimental drug limited by Federal Law to Investigational Use Only".

Shipping to the clinical to the Clinical sites will be performed using a LN2 dry shipper.

Example 6: Storage of Cells at Clinical Site and Preparing Cells for Administration The cryopreserved products will be stored as needed at Clinical sites who have long term LN2 storage available. For other sites the products will remain in the LN2 dry shipper and scheduled to arrive the day prior to infusion.

Upon request, the appropriate number of released, frozen bags will be thawed in a 37±1° C. water bath. In a BSC, the cell suspension will be transferred to conical tubes and slowly diluted with a PBS buffer or Plasmalyte A supplemented with 1% human serum albumin. The diluted suspension will be centrifuged and the cell pellet suspended in the dilution buffer. The cells will be counted to determine total viability. The cells will be centrifuged and the cell pellet resuspended in buffer to the final cell concentration.

Example 7: Clinical Indication: Heart Failure Through Delivery of Culture Expanded NK-1R Positive Cells Cells prepared and provided according to examples 1, 2, 3, 4, and 5 are available for delivery to the heart at a dosage of 200 million cells in ten 0.5 cc doses, delivered through the BioCardia Helix transendocardial biotherapeutic delivery system to ten locations around regions of infarction in the heart identified by correlating previous imaging modalities to the fluoroscopy in the interventional cardiology suite. Prior to each delivery engagement of the needle delivery system to the heart is confirmed by delivering a small amount of contrast through the base of the needle, and after confirmation 0.5 cc of carrier phosphate buffered saline containing 20 million NK1R+ cells is infused intramyocardially. After the tenth delivery, the delivery system is removed.

Example 8: Clinical Indication: Local Joint Pain Treatment Through Infusion of Culture Expansion of NK1R+ Cells Cells prepared and provided to a subject according to examples 1, 2, 3, 4, and 5 are available for delivery to the ankle, knee, hip, spine, neck, shoulder, or elbow at a dosage of 100 to 500 million cells in one or more infusions into the site of pain in a carrier of plasmalyte.

Example 9: Clinical Indication: Rheumatoid Arthritis Therapy Through Injection of Culture Expanded NK1R+ Cells Cells prepared and provided to subject according to examples 1, 2, 3, 4, and 5 are available for delivery to the ankle, knee, hip, spine, neck, shoulder, or elbow at a dosage of 100 to 500 million cells in one or more infusions into the site of pain in a carrier of plasmalyte.

Example 10: Stroke Therapy Through Carotid Infusion of Culture Expanded NK1R+ Cells Cells are prepared and delivered into a catheter that resides in the internal or external carotid arteries through a standard vascular access catheter system. The cells are delivered at a dose of 100 to 200M cells through a filter in line with the catheter to prevent cell aggregation induced emboli.

Example 11: Diabetes Therapy Via Intravascular Infusion of Culture Expanded NK1R+ Cells Cells are prepared and delivered into a catheter that resides in the splenic artery through a standard vascular access catheter system. The cells are delivered at a dose of 100 to 200M cells through a filter in line with the catheter to prevent cell aggregation induced emboli.

Example 12: Diabetes Therapy Via Intrastitial Infusion of Culture Expanded NK1R+ Cells Cells are prepared and delivered into the pancreas by an interventional radiologist navigating a needle into the pancreas using ultrasound or fluoroscopic guidance. The cells are delivered at a dose of 100 to 200M cells.

Example 13: Asthma and Pulmonary Fibrosis Therapy by Intravenous Infusion of a Therapeutic Dosage of NK1R+ Cells Slow sustained intravenous infusion of cells is performed which results in the larger culture expanded NK1R+ cells being substantially trapped in the lungs.

Example 14: Aging

Repeated intravenous dosing of cells, combined with interstitial delivery to problem areas of pain or tissue damage.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating a disease or disorder comprising:
   isolating mesenchymal stem cells (MSCs) that express neurokinin-1 receptor (NK1R+ MSCs) from a bone marrow of a human subject by using an antibody to NK1R; and
   administering to a patient a therapeutically effective amount of the NK1R+ MSCs to treat the diseases or disorders, wherein the disease or disorder is selected from the set of: cardiovascular disease, pain, rheumatoid arthritis, diabetes, stroke, asthma, pulmonary fibrosis, and aging.

2. The method of claim 1, wherein the NK1R+ MSCs are isolated from donors comprising: autologous, syngeneic, allogeneic, or xenogeneic.

3. The method of claim 1, wherein the NK1R+ MSCs differentiate after administration into at least one lineage comprising: myocardial, vascular, or endothelial lineages.

4. The method of claim 3, wherein the NK1R+ MSCs that differentiate into myocardial lineage are identifiable by markers comprising: GATA-4, Nkx2.5 or sarcomeric actin.

5. The method of claim 3, wherein the NK1R+ MSCs that differentiate into vascular lineage are identifiable by markers comprising: smooth muscle actin or SMA22.

6. The method of claim 3, wherein the NK1R+ MSCs that differentiate into endothelial lineage are identifiable by markers comprising: CD31 or vimentin.

7. The method of claim 1, wherein one or more agents are administered to the patient, the agents comprising at least one of: cytokines, chemotactic factors, growth factors, or differentiation factors.

8. The method of claim 1, wherein the NK1R+ MSCs are administered to a patient in varying concentrations over a period of time.

9. The method of claim 1, wherein the disease or disorder is a cardiovascular disease and the NK1R+ MSCs are engrafted in a heart in vivo in infarct and border zones.

10. The method of claim 1, wherein the NK1R+ MSCs are conditioned with media conditioned by heart derived stromal cells.

11. The method of claim 1, wherein the NK1R+ MSCs are cultured and expanded ex vivo prior to the administering to the patient.

12. The method of claim 1, wherein the NK1R+ MSCs are freshly isolated.

13. The method of claim 11, wherein the NK1R+ MSCs are cultured in a hollow fiber bioreactor.

14. The method of claim 1, wherein the administrating step comprises delivering a dosage of 100 million to 500 million NK1R+ MSCs.

15. The method of claim 11, wherein the NK1R+ MSCs are cultured in a medium comprising substance P.

16. A method of treating a disease or disorder comprising:
   isolating mesenchymal stem cells (MSCs) that express neurokinin-1 receptor (NK1R+ MSCs) from a bone marrow of a human subject by using an antibody to NK1R;
   culturing and expanding the NK1R+ MSCs ex vivo; and
   administering to a patient a therapeutically effective amount of the NK1R+ MSCs to treat the diseases or disorders, wherein the disease or disorder is selected from the set of: cardiovascular disease, pain, rheumatoid arthritis, diabetes, stroke, asthma, pulmonary fibrosis, and aging.

\* \* \* \* \*